US008648109B2

(12) United States Patent
Leonard et al.

(10) Patent No.: US 8,648,109 B2
(45) Date of Patent: Feb. 11, 2014

(54) **FORMS OF [R-(R*,R*)]-2-(4-FLUOROPHENYL)-β,δ-DIHYDROXY-5-(1-METHYLETHYL)-3-PHENYL-4-[(PHENYLAMINO)CARBONYL]-1H-PYRROLE-1-HEPTANOIC ACID MAGNESIUM**

(71) Applicants: Jason Albert Leonard, New Rochelle, NY (US); Jonathan Mark Miller, Lindenhurst, IL (US)

(72) Inventors: Jason Albert Leonard, New Rochelle, NY (US); Jonathan Mark Miller, Lindenhurst, IL (US)

(73) Assignee: Warner-Lambert Company LLC, New York, NY (US)

( * ) Notice: Subject to any disclaimer, the term of this patent is extended or adjusted under 35 U.S.C. 154(b) by 0 days.

(21) Appl. No.: 13/746,815

(22) Filed: Jan. 22, 2013

(65) Prior Publication Data

US 2013/0131138 A1 May 23, 2013

Related U.S. Application Data

(62) Division of application No. 13/295,470, filed on Nov. 14, 2011, now Pat. No. 8,383,667, which is a division of application No. 12/094,296, filed as application No. PCT/IB2006/003239 on Nov. 9, 2006, now Pat. No. 8,084,488.

(60) Provisional application No. 60/738,447, filed on Nov. 21, 2005.

(51) Int. Cl.
*C07D 207/34* (2006.01)
*A61P 3/00* (2006.01)
*A61P 19/10* (2006.01)
*A61P 25/28* (2006.01)

(52) U.S. Cl.
USPC .......................................................... 514/423

(58) Field of Classification Search
USPC .......................................................... 514/12
See application file for complete search history.

(56) References Cited

U.S. PATENT DOCUMENTS

| | | | |
|---|---|---|---|
| 4,681,893 A | 7/1987 | Roth .............................. | 514/422 |
| 5,003,080 A | 3/1991 | Butler et al. ................... | 548/517 |
| 5,097,045 A | 3/1992 | Butler et al. ................... | 549/373 |
| 5,103,024 A | 4/1992 | Millar et al. ................... | 549/373 |
| 5,124,482 A | 6/1992 | Butler et al. ................... | 564/169 |
| 5,149,837 A | 9/1992 | Butler et al. ................... | 549/333 |
| 5,155,251 A | 10/1992 | Butler et al. ................... | 558/442 |
| 5,216,174 A | 6/1993 | Butler et al. ................... | 548/517 |
| 5,245,047 A | 9/1993 | Butler et al. ................... | 548/517 |
| 5,248,793 A | 9/1993 | Millar et al. ................... | 549/375 |
| 5,273,995 A | 12/1993 | Roth .............................. | 514/422 |
| 5,280,126 A | 1/1994 | Butler et al. ................... | 548/517 |
| 5,298,627 A | 3/1994 | Butler et al. ................... | 548/517 |
| 5,342,942 A | 8/1994 | Jaen et al. ...................... | 544/250 |
| 5,397,792 A | 3/1995 | Butler et al. ................... | 514/326 |
| 5,446,054 A | 8/1995 | Butler et al. ................... | 514/326 |
| 5,470,981 A | 11/1995 | Butler et al. ................... | 546/207 |
| 5,489,690 A | 2/1996 | Butler et al. ................... | 546/245 |
| 5,489,691 A | 2/1996 | Butler et al. ................... | 548/517 |
| 5,510,488 A | 4/1996 | Butler et al. ................... | 546/207 |
| 5,686,104 A | 11/1997 | Mills et al. ..................... | 424/451 |
| 5,969,156 A | 10/1999 | Briggs et al. ................... | 548/437 |
| 5,998,633 A | 12/1999 | Jacks et al. ..................... | 549/313 |
| 6,087,511 A | 7/2000 | Lin et al. ........................ | 548/537 |
| 6,121,461 A | 9/2000 | McKenzie ...................... | 548/530 |
| 6,126,971 A | 10/2000 | Mills et al. ..................... | 424/484 |
| 6,433,213 B1 | 8/2002 | Bosch et al. ................... | 558/441 |
| 6,476,235 B2 | 11/2002 | Butler et al. ................... | 548/517 |
| 6,528,660 B1 | 3/2003 | Kumar et al. ................... | 548/537 |
| 6,605,636 B2 | 8/2003 | Aronhime et al. .............. | 514/423 |
| 6,605,729 B1 | 8/2003 | Byrn et al. ...................... | 548/537 |
| 6,867,306 B2 | 3/2005 | Srinath et al. .................. | 548/517 |
| 6,891,047 B2 | 5/2005 | Pflaum ........................... | 548/537 |
| 7,030,151 B2 | 4/2006 | Kerc et al. ...................... | 514/422 |
| 7,074,940 B2 | 7/2006 | Sorsak ............................ | 548/537 |
| 7,342,120 B2 | 3/2008 | Aronhime et al. .............. | 548/537 |
| 7,361,772 B2 | 4/2008 | Mathew et al. ................. | 548/537 |
| 2003/0175338 A1 | 9/2003 | Singh et al. .................... | 424/465 |
| 2004/0063969 A1 | 4/2004 | Greff et al. ..................... | 548/537 |
| 2005/0209306 A1 | 9/2005 | Jegorov et al. ................. | 514/423 |
| 2006/0122403 A1 | 6/2006 | Suri et al. ....................... | 548/537 |
| 2006/0205805 A1 | 9/2006 | Van Der Schaaf et al. ... | 514/423 |

FOREIGN PATENT DOCUMENTS

| | | | | |
|---|---|---|---|---|
| EP | 1336405 | 8/2003 | .............. | A61K 9/14 |
| WO | WO 0136384 | 5/2001 | ......... | C07D 207/335 |
| WO | WO 02057228 | 7/2002 | ........... | C07D 207/34 |
| WO | WO 02083637 | 10/2002 | ........... | C07D 207/34 |
| WO | WO 02083638 | 10/2002 | | |
| WO | WO 2006008091 | 1/2006 | ........... | C07D 498/14 |
| WO | WO 2006054308 | 5/2006 | ........... | A61K 31/401 |
| WO | WO 2006070248 | 7/2006 | .............. | A61K 9/20 |
| WO | WO 2006084474 | 8/2006 | | |
| WO | WO 2006117761 | 11/2006 | | |
| WO | WO 2007132472 | 11/2007 | ......... | C07D 207/335 |

OTHER PUBLICATIONS

Chen, X., et al., Quantifying amorphous content of lactose using parallel beam X-ray powder diffraction and whole pattern fitting, *J. Pharmacetical and Biomedical Analysis*, vol. 26, pp. 63, (2001).

(Continued)

*Primary Examiner* — San-Ming Hui
*Assistant Examiner* — Kathrien Cruz
(74) *Attorney, Agent, or Firm* — Francis J. Tinney

(57) ABSTRACT

Novel forms of atorvastatin magnesium salt designated Form A, Form B, Form C, Form D, Form E, and Form F, pharmaceutical compositions containing such compounds, methods for their preparation and methods utilizing the compounds for treatment of hyperlipidemia, hypercholesterolemia, osteoporosis, benign prostatic hyperplasia (BPH) and Alzheimer's disease are described.

25 Claims, 18 Drawing Sheets

(56) References Cited

OTHER PUBLICATIONS

Hancock, B. C., et al., Comparison of the mechanical properties of the crystalline and amorphous forms of a drug substance, *International Journal of Pharmaceutics*, vol. 241, pp. 73-85, (2002).

Hiestand, H. E. N., et al., Indices of Tableting Performance, *Powder Technology*, vol. 38, pp. 145-159, (1984).

Konno, T., Physical and Chemical Changes of Medicinals in Mixtures with Absorbents in the Solid State. IV. Study on Reduced-Pressure Mixing for Practical Use of Amorphous Mixtures of Flufenamic Acid, *Chem. Pharm. Bull.*, vol. 38, No. 7, pp. 2002-2007 (1990).

Description of manufacturing method for preparing atorvastatin magnesium according to example 3 of WO 2007/132472.

Description of manufacturing method for preparing atorvastatin magnesium according to example 2 of WO 2006/117761.

13C solid state NMR spectrum of the pure atorvastatin magnesium obtained in example 10 of US 5,273,995.

13C solid state NMR spectrum of the crude atorvastatin magnesium obtained in example 10 of US 5,273,995.

Description of manufacturing method for preparing atorvastatin magnesium according to example 10 of US 5,273,995.

Caira, M. R., et al., *Topics in Current Chemistry*, vol. 198, pp. 163-208, (1998).

Statement of Opposition (including these documents): Priority document for WO 2006/117761 Excerpt from British Pharmacopeia, 1993; Declaration of Dr. Ron Lawrence dated Feb. 4, 2011; Pharmaceutical Production—An Engineering Guide, Eds. B. Bennett and G. Cole, IChemE, 2003, pp. 85-96 Vogel's Textbook of Practical Organic Chemistry—Fifth Edition, Eds. B. S. Furnis et al., Pearson Prentice Hall, 1989, pp. 131-1333 Handbook of Pharmaceutical Salts—Properties, Selection and Use, Eds. P. H. Stahl and G. Wermuth, Verlay Helvetica Chimica Acta, 2002, pp. 67-74.

FORMS OF [R-(R*,R*)]-2-(4-FLUOROPHENYL)-β,δ-DIHYDROXY-5-(1-METHYLETHYL)-3-PHENYL-4-[(PHENYLAMINO)CARBONYL]-1H-PYRROLE-1-HEPTANOIC ACID MAGNESIUM

This application is a divisional application of U.S. Ser. No. 13/295,470 filed on Nov. 14, 2011, which is a divisional application of U.S. Ser. No. 12/094,296 filed on Sep. 2, 2008, now U.S. Pat. No. 8,084,488, which is a 371 application of PCT/IB2006/003239 filed on Nov. 9, 2006, which claims benefit of provisional application U.S. Ser. No. 60/738,447 filed on Nov. 21, 2005, all of which are incorporated herein by reference in their entirety.

FIELD OF THE INVENTION

The present invention relates to Novel forms of [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid magnesium salt designated Form A, Form B, Form C, Form D, Form E, and Form F, characterized by one or more of their X-ray powder diffraction, solid state NMR carbon chemical shift, and solid state NMR fluorine chemical shift. The present invention also relates to pharmaceutical compositions containing such compounds, methods for their preparation and methods for their use in the treatment of hyperlipidemia, hypercholesterolemia, osteoporosis, benign prostatic hyperplasia (BPH) and Alzheimer's disease.

BACKGROUND OF THE INVENTION

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid lowering agents. Atorvastatin calcium, disclosed in U.S. Pat. No. 5,273,995, which is incorporated herein by reference, is currently sold as LIPITOR® having the chemical name [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) trihydrate.

Atorvastatin calcium is a selective, competitive inhibitor of HMG-CoA reductase. As such, atorvastatin calcium is a potent lipid lowering compound and is thus useful as a hypolipidemic and/or hypocholesterolemic agent.

A number of patents have issued disclosing atorvastatin, formulations of atorvastatin, as well as processes and key intermediates for preparing atorvastatin. These include: U.S. Pat. Nos. 4,681,893; 5,273,995; 5,003,080; 5,097,045; 5,103,024; 5,124,482; 5,149,837; 5,155,251; 5,216,174; 5,245,047; 5,248,793; 5,280,126; 5,397,792; 5,342,952; 5,298,627; 5,446,054; 5,470,981; 5,489,690; 5,489,691; 5,510,488; 5,686,104; 5,998,633; 6,087,511; 6,126,971; 6,433,213; and 6,476,235, which are herein incorporated by reference.

Additionally, a number of published International Patent Applications and patents have disclosed crystalline forms of atorvastatin, as well as processes for preparing amorphous atorvastatin. These include: U.S. Pat. No. 5,969,156; U.S. Pat. No. 6,121,461;U.S. Pat. No. 6,605,729; WO 00/71116; WO 01/28999; WO 01/36384; WO 01/42209; WO 02/41834; WO 02/43667; WO 02/43732; WO 02/051804; WO 02/057228; WO 02/057229; WO 02/057274; WO 02/059087; WO 02/072073; WO 02/083637; WO 02/083638; WO 03/050085; WO 03/070702; and WO 04/022053.

Atorvastatin is prepared as its calcium salt, i.e., [R—(R*,R*)]-2-(4-fluorophenyl)-β,δ-dihydroxy-5-(1-methylethyl)-3-phenyl-4-[(phenylamino)-carbonyl]-1H-pyrrole-1-heptanoic acid calcium salt (2:1). The calcium salt is desirable, since it enables atorvastatin to be conveniently formulated in, for example, tablets, capsules, lozenges, powders, and the like for oral administration.

The process by which atorvastatin calcium is produced needs to be one which is amenable to large-scale production. Additionally, it is desirable that the product should be in a form that is readily filterable and easily dried. Finally, it is economically desirable that the product be stable for extended periods of time without the need for specialized storage conditions.

Furthermore, it has been disclosed that the amorphous forms in a number of drugs exhibit different dissolution characteristics, and in some cases different bioavailability patterns compared to the crystalline forms (Konno T., Chem. Pharm. Bull., 1990; 38; 2003-2007). For some therapeutic indications, one bioavailability pattern may be favored over another.

In the course of drug development, it is generally assumed to be important to discover the most stable crystalline form of the drug. This most stable crystalline form is the form which is likely to have the best chemical stability, and thus the longest shelf-life in a formulation. However, it is also advantageous to have multiple forms of a drug, e.g. salts, hydrates, polymorphs, crystalline, and noncrystalline forms. There is no one ideal physical form of a drug because different physical forms provide different advantages. The search for the most stable form and for such other forms is arduous and the outcome is unpredictable.

The successful development of a drug requires that it meet certain requirements to be a therapeutically effective treatment for patients. These requirements fall into two categories: (1) requirements for successful manufacture of dosage forms, and (2) requirements for successful drug delivery and disposition after the drug formulation has been administered to the patient.

There are many kinds of drug formulations for administration by various routes, and the optimum drug form for different formulations is likely to be different. As mentioned above, a drug formulation must have sufficient shelf-life to allow successful distribution to patients in need of treatment. In addition, a drug formulation must provide the drug in a form which will dissolve in the patient's gastrointestinal tract when orally dosed. For oral dosing in an immediate release dosage form, such as an immediate release tablet, capsule, suspension, or sachet, it is generally desirable to have a drug salt or drug form which has high solubility, in order to assure complete dissolution of the dose and optimal bioavailability. For some drugs, particularly low solubility drugs or poorly wetting drugs, it may be advantageous to utilize a noncrystalline drug form, which will generally have a higher initial solubility than a crystalline form when administered into the gastrointestinal tract. A noncrystalline form of a drug is frequently less chemically stable than a crystalline form. Thus, it is advantageous to identify noncrystalline drug forms which are sufficiently chemically stable to provide a practical product which is stable enough to maintain its potency for enough time to permit dosage form manufacture, packaging, storage, and distribution to patients around the world.

On the other hand, there are dosage forms which operate better if the drug form is less soluble. For example, a chewable tablet or a suspension or a sachet dosage form exposes the tongue to the drug directly. For such dosage forms, it is desirable to minimize the solubility of the drug in the mouth, in order to keep a portion of the drug in the solid state, minimizing bad taste. For such dosage forms, it is often desirable to use a low solubility salt or crystalline form.

For controlled release oral or injectable, e.g. subcutaneous or intramuscular, dosage forms, the desired drug solubility is a complex function of delivery route, dose, dosage form design, and desired duration of release. For a drug which has high solubility, it may be desirable to utilize a lower solubility crystalline salt or polymorph for a controlled release dosage form, to aid in achievement of slow release through slow dissolution. For a drug which has low solubility, it may be necessary to utilize a higher solubility crystalline salt or polymorph, or a noncrystalline form, in order to achieve a sufficient dissolution rate to support the desired drug release rate from the controlled release dosage form.

In soft gelatin capsule dosage forms ("soft-gels"), the drug is dissolved in a small quantity of a solvent or vehicle such as a triglyceride oil or polyethylene glycol, and encapsulated in a gelatin capsule. An optimal drug form for this dosage form is one which has a high solubility in an appropriate soft-gel vehicle. In general, a drug form which is more soluble in a triglyceride oil will be less soluble in water. Identification of an appropriate drug form for a soft-gel dosage form requires study of various salts, polymorphs, crystalline, and noncrystalline forms.

Thus, it can be seen that the desired solubility of a drug form depends on the intended use, and not all drug forms are equivalent.

For a drug form to be practically useful for human or animal therapy, it is desirable that the drug form exhibit minimal hygroscopicity. Dosage forms containing highly hygroscopic drugs require protective packaging, and may exhibit altered dissolution if stored in a humid environment. Thus, it is desirable to identify nonhygroscopic crystalline salts and polymorphs of a drug. If a drug is noncrystalline, or if a noncrystalline form is desired to improve solubility and dissolution rate, then it is desirable to identify a noncrystalline salt or form which has a low hygroscopicity relative to other noncrystalline salts or forms.

A drug, crystalline or noncrystalline, may exist in an anhydrous form, or as a hydrate or solvate or hydrate/solvate. The hydration state and solvation state of a drug affects its solubility and dissolution behavior.

The melting point of a drug may vary for different salts, polymorphs, crystalline, and noncrystalline forms. In order to permit manufacture of tablets on commercial tablet presses, it is desirable that the drug melting point be greater than around 60° C., preferably greater than 100° C. to prevent drug melting during tablet manufacture. A preferred drug form in this instance is one that has the highest melting point. In addition, it is desirable to have a high melting point to assure chemical stability of a solid drug in a solid dosage form at high environmental storage temperatures which occur in direct sunlight and in geographic areas such as near the equator. If a soft-gel dosage form is desired, it is preferred to have a drug form which has a low melting point, to minimize crystallization of the drug in the dosage form. Thus, it can be seen that the desired melting point of a drug form depends on the intended use, and not all drug forms are equivalent.

When a drug's dose is high, or if a small dosage form is desired, the selection of a salt, hydrate, or solvate affects the potency per unit weight. For example, a drug salt with a higher molecular weight counterion will have a lower drug potency per gram than will a drug salt with a lower molecular weight counterion. It is desirable to choose a drug form which has the highest potency per unit weight. The method of preparation of different crystalline polymorphs and noncrystalline forms varies widely from drug to drug. It is desirable that minimally toxic solvents be used in these methods, particularly for the last synthetic step, and particularly if the drug has a tendency to exist as a solvate with the solvent utilized in the last step of synthesis. Preferred drug forms are those which utilize less toxic solvents in their synthesis.

The ability of a drug to form good tablets at commercial scale depends upon a variety of drug physical properties, such as the Tableting Indices described in Hiestand H, Smith D. Indices of tableting performance. Powder Technology, 1984; 38:145-159. These indices may be used to identify forms of a drug, e.g. of atorvastatin calcium, which have superior tableting performance. One such index is the Brittle Fracture Index (BFI), which reflects brittleness, and ranges from 0 (good-low brittleness) to 1 (poor-high brittleness). Other useful indices or measures of mechanical properties, flow properties, and tableting performance include compression stress, absolute density, solid fraction, dynamic indentation hardness, ductility, elastic modulus, reduced elastic modulus, quasistatic indentation hardness, shear modulus, tensile strength, compromised tensile strength, best case bonding index, worst case bonding index, brittle/viscoelastic bonding index, strain index, viscoelastic number, effective angle of internal friction (from a shear cell test), cohesivity (from a powder avalanche test), and flow variability. A number of these measures are obtained on drug compacts, preferably prepared using a triaxial hydraulic press. Many of these measures are further described in Hancock B, Carlson G, Ladipo D, Langdon B, and Mullarney M. Comparison of the Mechanical Properties of the Crystalline and Amorphous Forms of a Drug Substance. International Journal of Pharmaceutics, 2002; 241:73-85.

Drug form properties which affect flow are important not just for tablet dosage form manufacture, but also for manufacture of capsules, suspensions, and sachets.

The particle size distribution of a drug powder can also have large effects on manufacturing processes, particularly through effects on powder flow. Different drug forms have different characteristic particle size distributions.

From the above discussion, it is apparent that there is no one drug form which is ideal for all therapeutic applications. Thus it is important to seek a variety of unique drug forms, e.g. salts, polymorphs, noncrystalline forms, which may be used in various formulations. The selection of a drug form for a specific formulation or therapeutic application requires consideration of a variety of properties, as described above, and the best form for a particular application may be one which has one specific important good property while other properties may be acceptable or marginally acceptable.

The present invention answers the need by providing novel forms of atorvastatin magnesium. Thus the present invention provides new forms of atorvastatin magnesium designated Forms A, B, C, D, E, and F. The new forms of atorvastatin magnesium disclosed in the present application offer the advantage of high water solubility. This is an advantage for immediate release dosage forms since such forms need to be fully dissolved in the stomach before passing into the digestive tract.

SUMMARY OF THE INVENTION

In a first aspect, the present invention comprises a Form A atorvastatin magnesium having one or more of characteristics selected from the group consisting of:

I) an X-ray powder diffraction containing the following 2θ values measured using CuK$_a$ radiation: 9.3, 14.3, and 18.4;

II) a $^{13}$C shift containing the values: 118.7, 124.4, 140.3, and 141.7 ppm; and III) an $^{19}$F shift containing the values: −108.4, and −112.6 ppm. As described herein, the x-ray powder diffraction (XRPD) pattern is expressed in terms of degree 2θ and relative intensities with a relative intensity of >10% and relative peak width measured on a Bruker D8 Discover X-ray powder diffractometer with GADDS (General Area Diffraction Detector System) CS (available from Bruker AXS, Inc., 5465 East Cheryl Parkway, Madison, Wis.) operating in reflection mode using CuK$_a$ radiation (1.54 Å). Furthermore, in each aspect, the invention encompasses experimental deviation in the 2θ and the shift values described herein; including the deviation ±0.2° 2θ as provided in X-ray powder diffraction (XPRD) Tables 1-7, and deviation ±0.2 ppm as provided in solid state nuclear magnetic resonance (SSNMR) Tables 8-19 below. Based on the descriptions set forth herein, such experimental deviation in the 2θ and the shift values can be readily determined by the ordinarily skilled artisan.

In one embodiment, the Form A atorvastatin magnesium of the invention has an X-ray powder diffraction containing the following 2θ values measured using CuK$_a$ radiation: 9.3, 11.7, 14.3, and 18.4

In another embodiment, the Form A atorvastatin magnesium of the invention has an X-ray powder diffraction containing the 2θ values measured using CuK$_a$ radiation as set forth in Table 1 and Table 7 below.

In another embodiment, the Form A atorvastatin magnesium of the invention has a solid state NMR shift selected from the group consisting of:

A) a $^{13}$C shift containing the values: 118.7, 124.4, 140.3, and 141.7 ppm; and B) an $^{19}$F shift containing the values: −108.4, and −112.6 ppm.

In another embodiment, the Form A atorvastatin magnesium of the invention has a $^{13}$C shift containing the values: 118.7, 124.4, 140.3, and 141.7 ppm.

In another embodiment, the Form A atorvastatin magnesium of the invention has a $^{13}$C shift containing the values set forth in Table 8.

In another embodiment, the Form A atorvastatin magnesium of the invention has a an $^{19}$F shift containing the values: −108.4, and −112.6 ppm.

In another embodiment, the Form A atorvastatin magnesium of the invention has an X-ray powder diffraction containing the following 2θ values measured using CuK$_a$ radiation: 9.3, 14.3, and 18.4; a $^{13}$C shift containing the values: 118.7, 124.4, 140.3, and 141.7 ppm; and an $^{19}$F shift containing the values: −108.4, and −112.6 ppm.

In a second aspect, the present invention is directed to Form B atorvastatin magnesium characterized by x-ray powder diffraction (XRPD) pattern expressed in terms of degree 2θ and relative intensities with a relative intensity of >10% and relative peak width measured on a Bruker D8 Discover X-ray powder diffractometer with GADDS (General Area Diffraction Detector System) CS operating in reflection mode using CuK$_a$ radiation (1.54 Å) as set forth in Table 2 and Table 7 below.

In a third aspect, the present invention is directed to Form C atorvastatin magnesium characterized by x-ray powder diffraction (XRPD) pattern expressed in terms of degree 2θ and relative intensities with a relative intensity of >10% and relative peak width measured on a Bruker D8 Discover X-ray powder diffractometer with GADDS (General Area Diffraction Detector System) CS operating in reflection mode using CuK$_a$ radiation (1.54 Å) as set forth in Table 3 and Table 7 below.

In a fourth aspect, the present invention is directed to Form D atorvastatin magnesium characterized by x-ray powder diffraction (XRPD) pattern expressed in terms of degree 2θ and relative intensities with a relative intensity of >10% and relative peak width measured on a Bruker D8 Discover X-ray powder diffractometer with GADDS (General Area Diffraction Detector System) CS operating in reflection mode using CuK$_a$ radiation (1.54 Å) as set forth in Table 4 and Table 7 below.

In a fifth aspect, the present invention is directed to Form E atorvastatin magnesium characterized by x-ray powder diffraction (XRPD) pattern expressed in terms of degree 2θ and relative intensities with a relative intensity of >10% and relative peak width measured on a Bruker D8 Discover X-ray powder diffractometer with GADDS (General Area Diffraction Detector System) CS operating in reflection mode using CuK$_a$ radiation (1.54 Å) as set forth in Table 5 and Table 7 below.

In a sixth aspect, the present invention is directed to Form F atorvastatin magnesium characterized by x-ray powder diffraction (XRPD) pattern expressed in terms of degree 2θ and relative intensities with a relative intensity of >10% and relative peak width measured on a Bruker D8 Discover X-ray powder diffractometer with GADDS (General Area Diffraction Detector System) CS operating in reflection mode using CuK$_a$ radiation (1.54 Å) as set forth in Table 6 and Table 7 below.

A further embodiment of the invention is a pharmaceutical composition comprising Form A, B, C, D, E, or F of atorvastatin magnesium in admixture with at least one pharmaceutically acceptable excipient, diluent, or carrier, each as described herein. The atorvastatin magnesium Forms A, B, C, D, E and F disclosed herein may be used in the treatments and regimens and at the dosage ranges for which atorvastatin calcium (LIPITOR®) is known in the art to be useful. As inhibitors of HMG-CoA reductase, Forms A, B, C, D, E, and F of atorvastatin magnesium are useful as hypolipidemic and hypocholesterolemic agents as well as agents in the treatment of osteoporosis, benign prostatic hyperplasia (BPH), and Alzheimer's disease. Accordingly, a still further embodiment of the present invention is a method of treating hyperlipidemia, hypercholesterolemia, osteoporsis, benign prostatic hyperplasia (BPH), and Alzheimer's disease comprising the step of administering to a patient suffering therefrom a therapeutically effective amount of Form A, Form B, Form C, Form D, Form E, or Form F atorvastatin magnesium, each as described herein, in unit dosage form.

The invention further provides for the use of Form A, Form B, Form C, Form D, Form E, or Form F atorvastatin magnesium, each as described herein, in the preparation of a medicament for the treatment of hyperlipidemia, hypercholesterolemia, osteoporosis, benign prostatic hyperplasia, or Alzheimer's disease. Also, the invention provides for the use of Form A, Form B, Form C, Form D, Form E, or Form F atorvastatin magnesium, or a combination of two or more of these forms, each as described herein, in the treatment of hyperlipidemia, hypercholesterolemia, osteoporosis, benign prostatic hyperplasia, or Alzheimer's disease.

Finally, the present invention is directed to methods for production of Form A, Form B, Form C, Form D, Form E, or Form F atorvastatin magnesium, each as described herein.

DETAILED DESCRIPTION OF THE INVENTION

Figure 1:
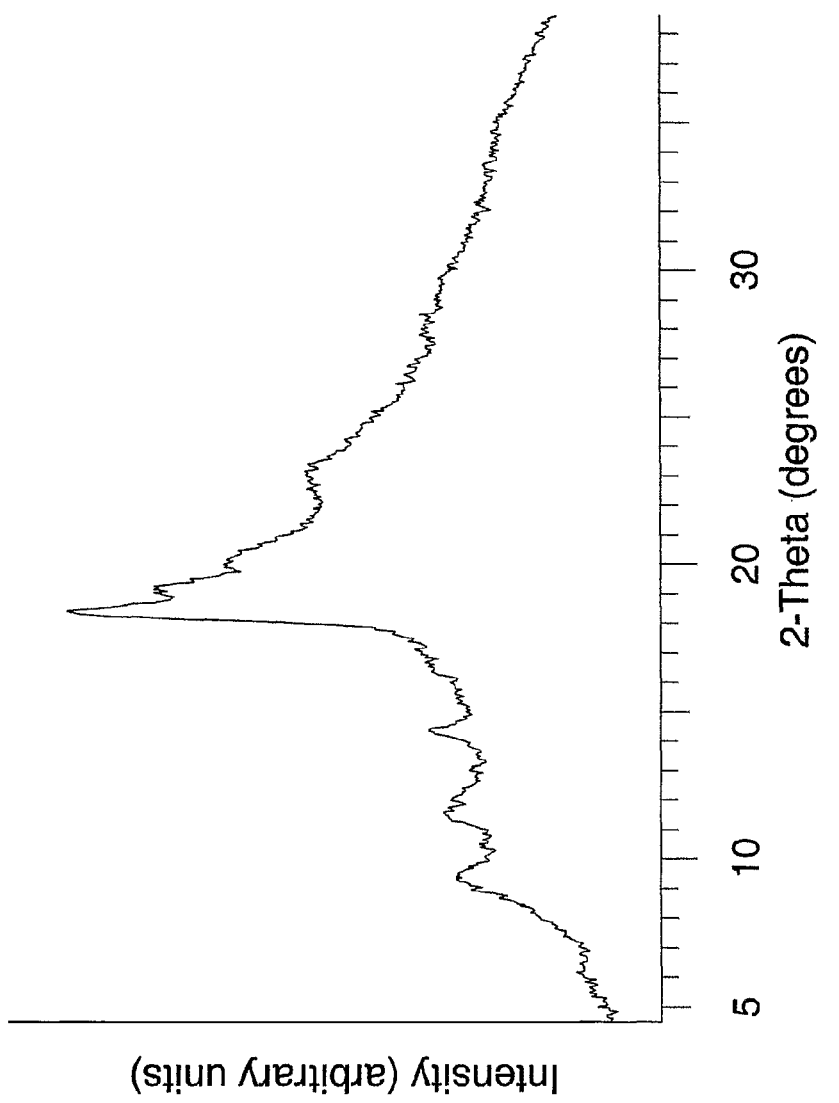
FIG. 1: Diffractogram of Form A atorvastatin magnesium measured on a Bruker D8 DISCOVER with GADDS (General Area Diffraction Detector System) CS X-ray powder diffractometer.
Figure 2:
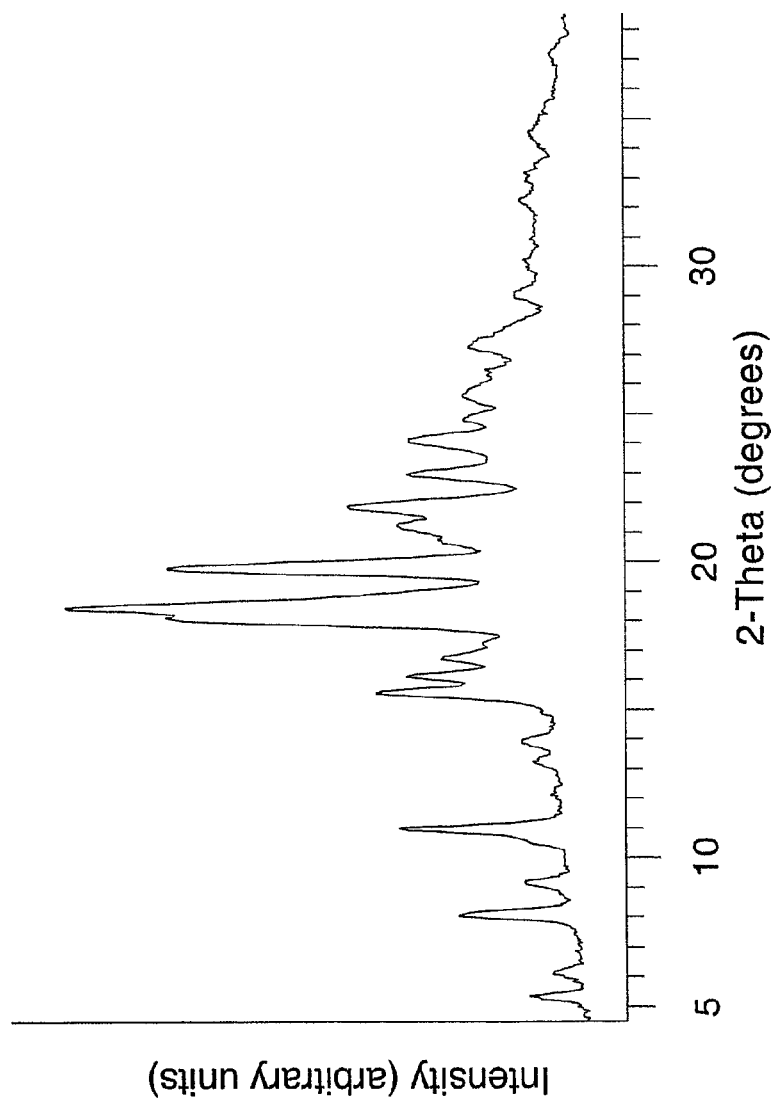
FIG. 2: Diffractogram of Form B atorvastatin magnesium measured on a Bruker D8 DISCOVER with GADDS CS X-ray powder diffractometer.
Figure 3:
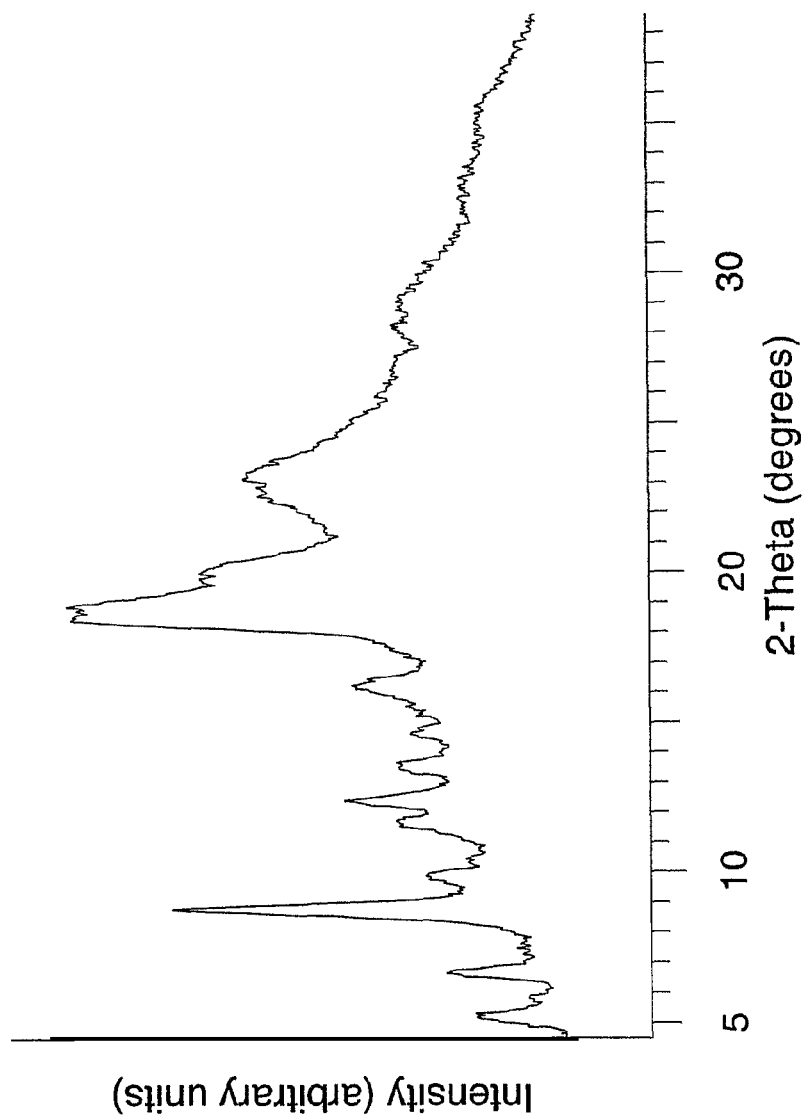
FIG. 3: Diffractogram of Form C atorvastatin magnesium measured on a Bruker D8 DISCOVER with GADDS CS X-ray powder diffractometer.
Figure 4:
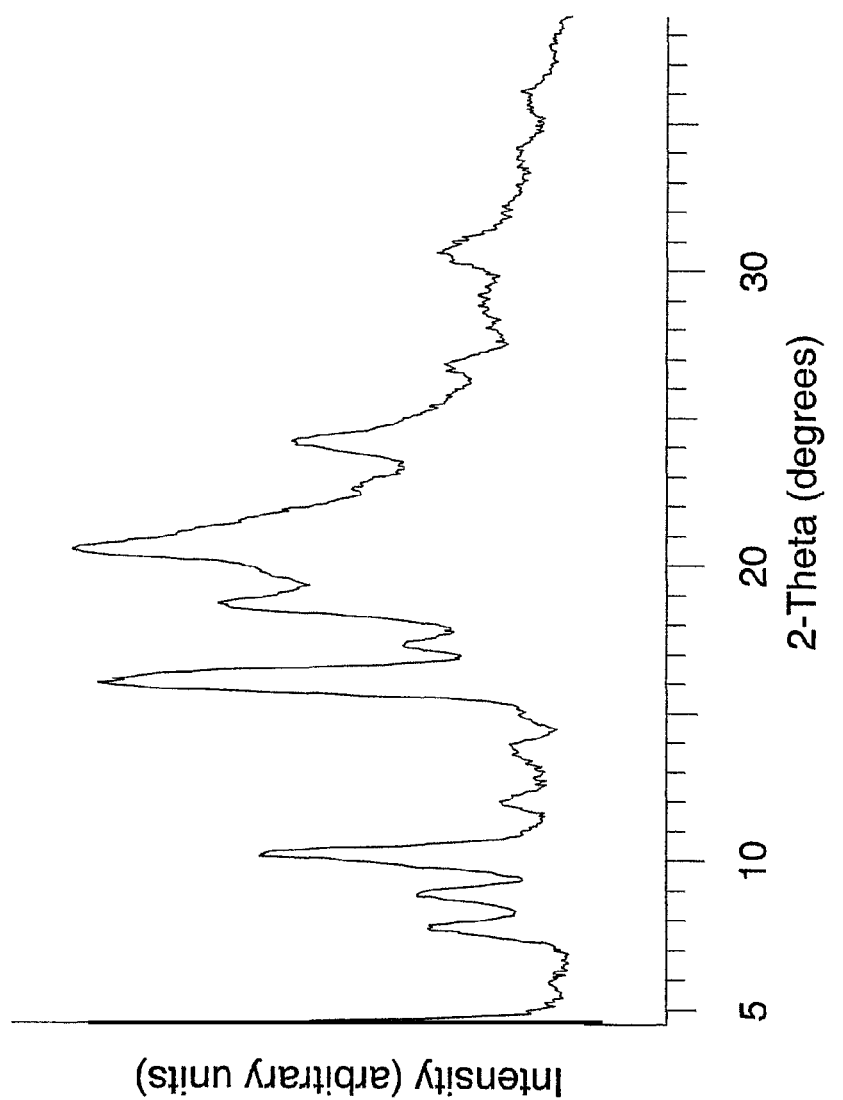
FIG. 4: Diffractogram of Form D atorvastatin magnesium measured on a Bruker D8 DISCOVER with GADDS CS X-ray powder diffractometer.
Figure 5:
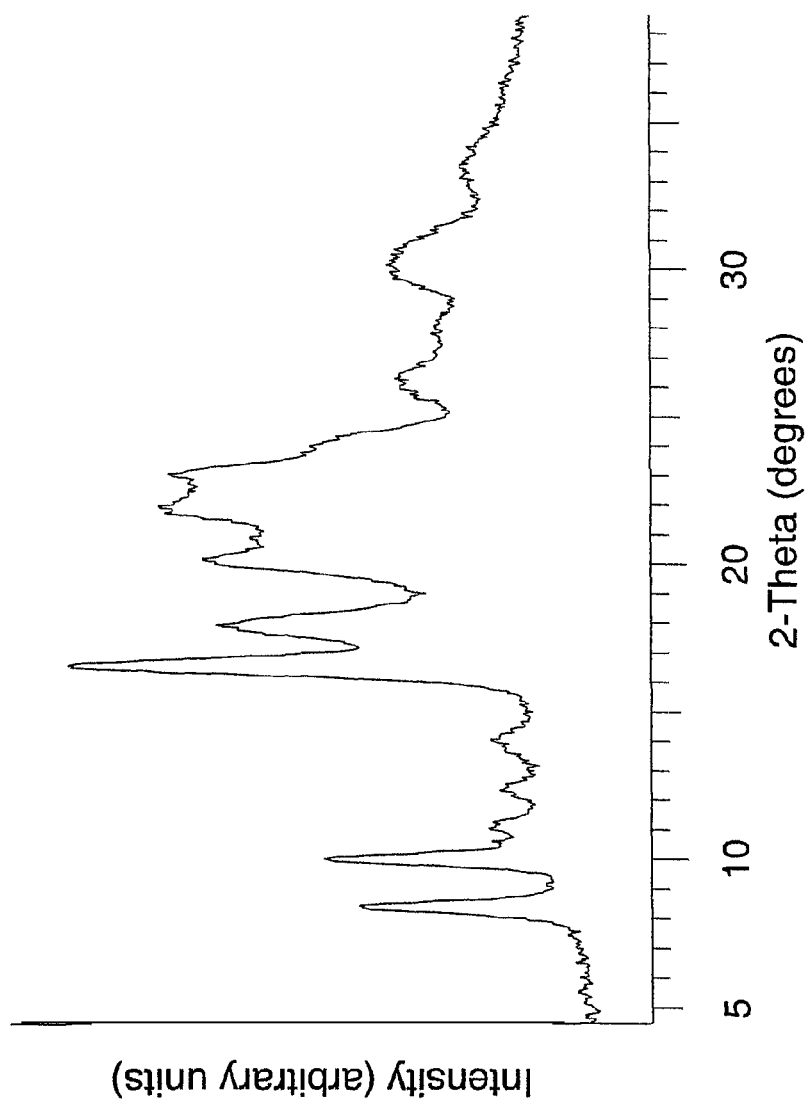
FIG. 5: Diffractogram of Form E atorvastatin magnesium measured on a Bruker D8 DISCOVER with GADDS CS X-ray powder diffractometer.
Figure 6:
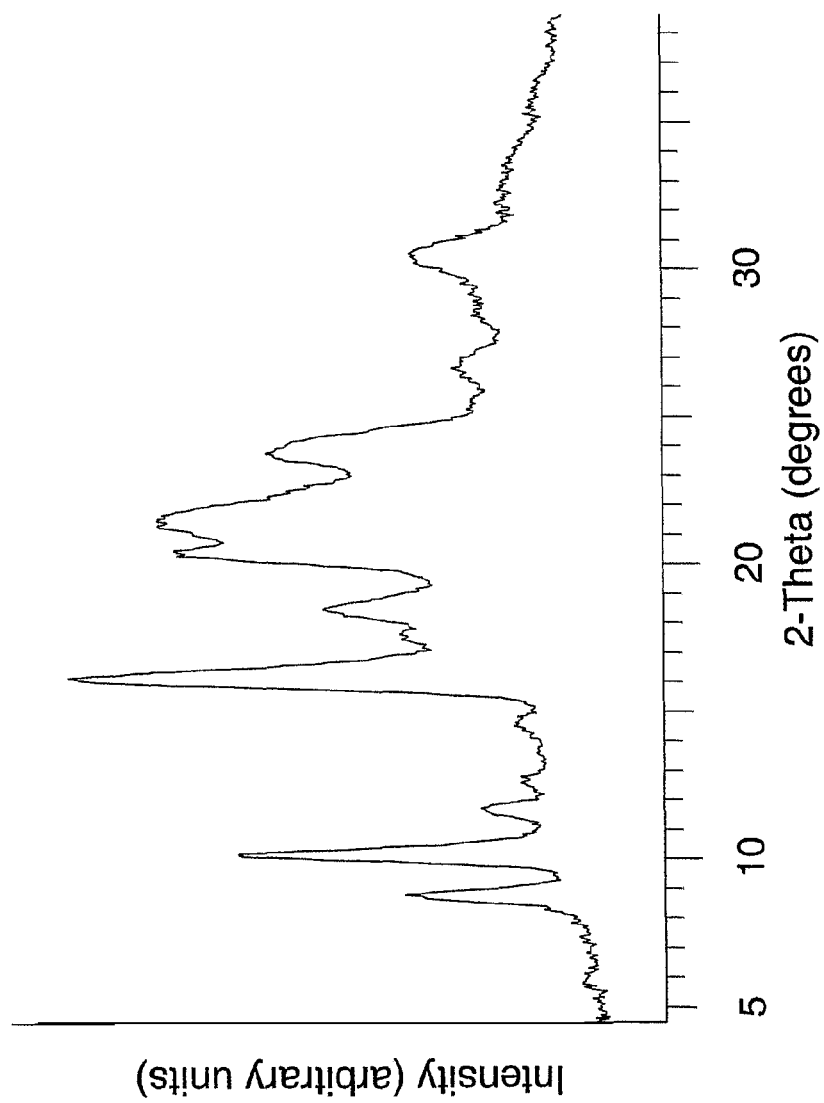
FIG. 6: Diffractogram of Form F atorvastatin magnesium measured on a Bruker D8 DISCOVER with GADDS CS X-ray powder diffractometer.
Figure 7:
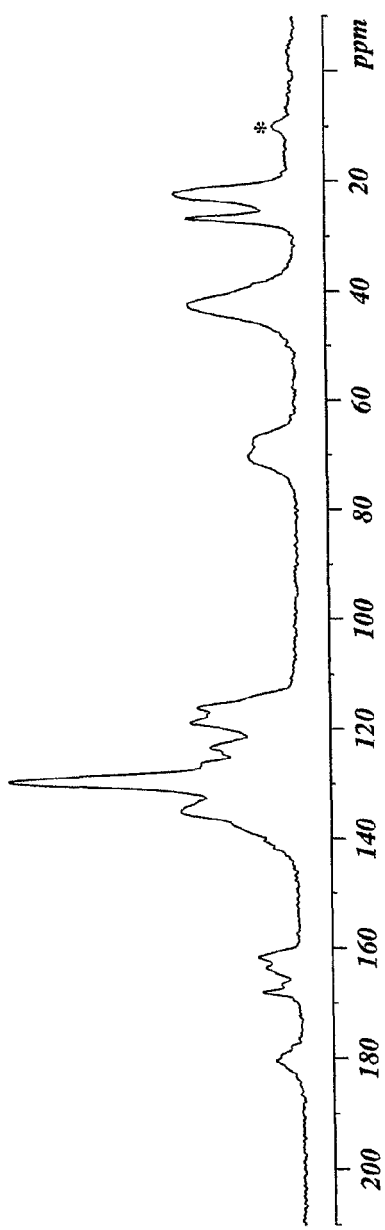
FIG. 7: Proton decoupled $^{13}$C CPMAS spectra of Form A atorvastatin magnesium. The peaks marked with an asterisk are spinning sidebands.
Figure 8:
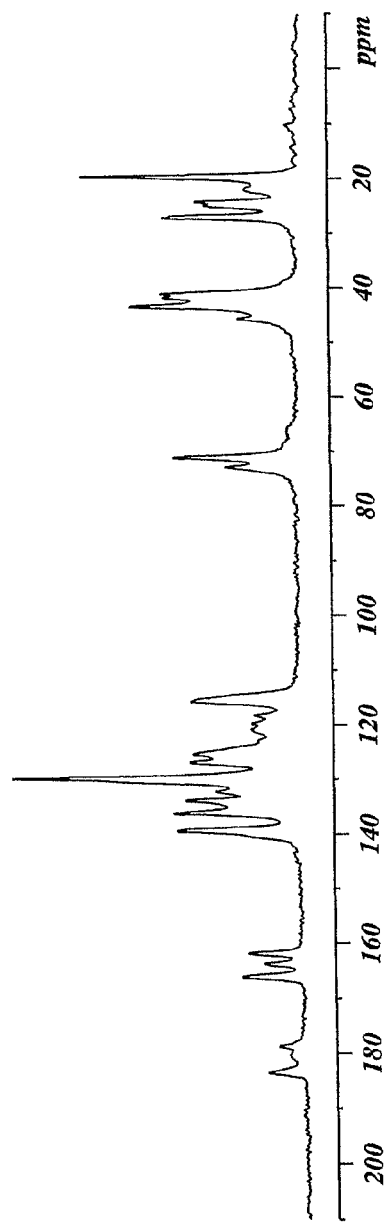
FIG. 8: Proton decoupled $^{13}$C CPMAS spectra of Form B atorvastatin magnesium. The peaks marked with an asterisk are spinning sidebands.
Figure 9:
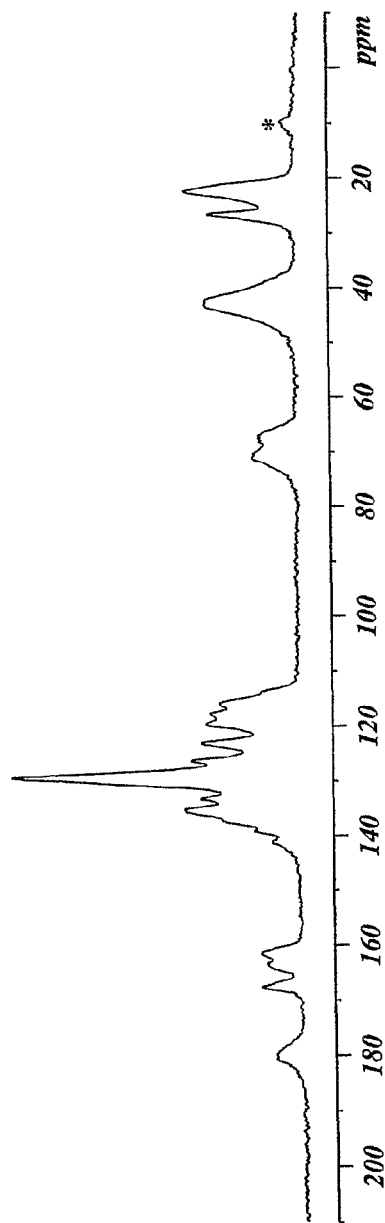
FIG. 9: Proton decoupled $^{13}$C CPMAS spectra of Form C atorvastatin magnesium. The peaks marked with an asterisk are spinning sidebands.
Figure 10:
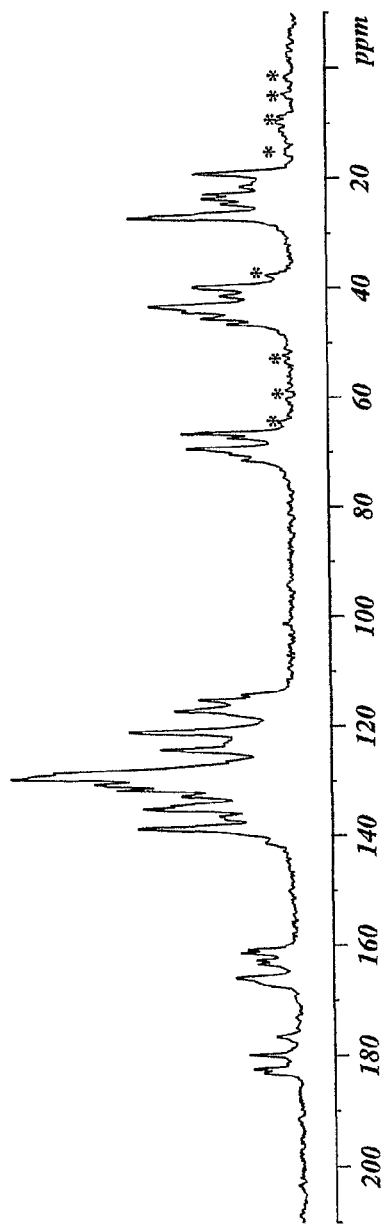
FIG. 10: Proton decoupled $^{13}$C CPMAS spectra of Form D atorvastatin magnesium. The peaks marked with an asterisk are spinning sidebands.
Figure 11:
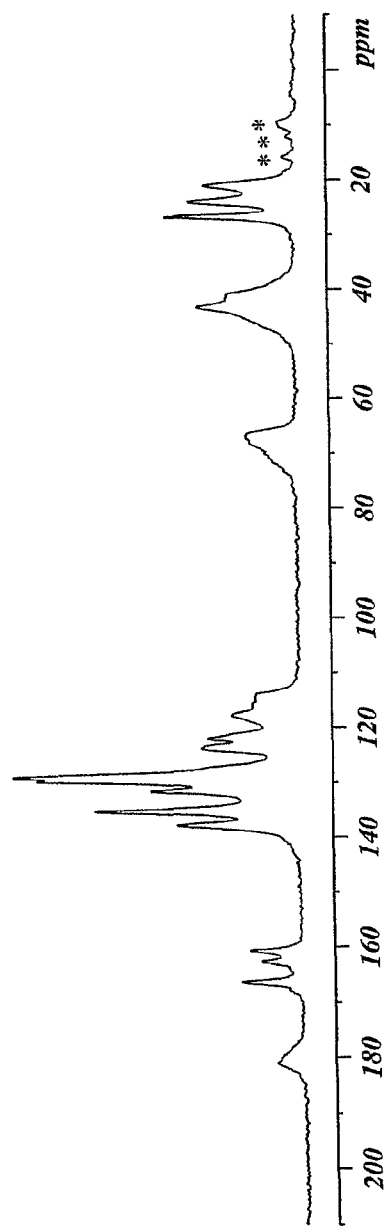
FIG. 11: Proton decoupled $^{13}$C CPMAS spectra of Form E atorvastatin magnesium. The peaks marked with an asterisk are spinning sidebands.
Figure 12:
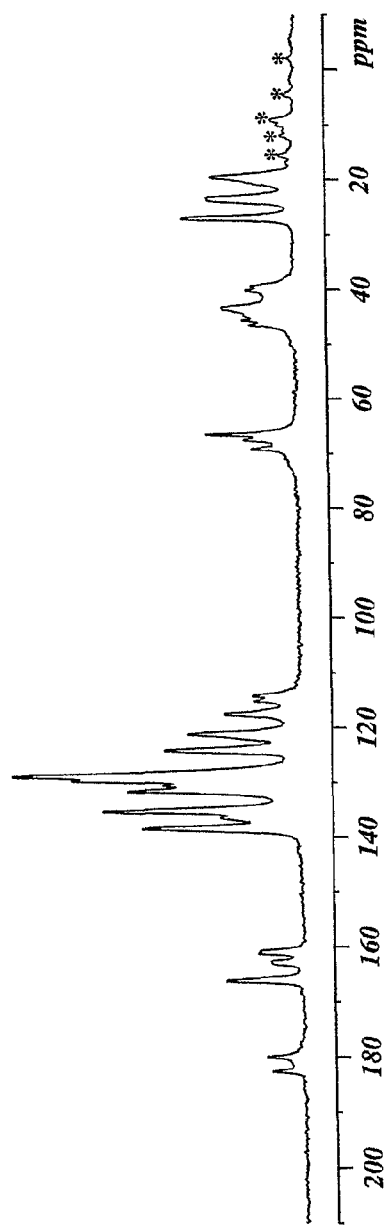
FIG. 12: Proton decoupled $^{13}$C CPMAS spectra of Form F atorvastatin magnesium. The peaks marked with an asterisk are spinning sidebands.
Figure 13:
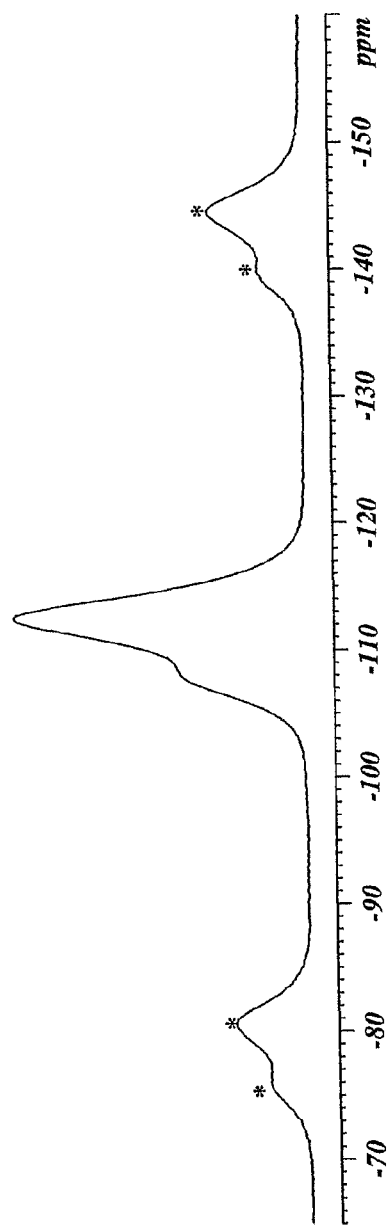
FIG. 13: Proton decoupled $^{19}$F MAS spectra of Form A atorvastatin magnesium. The peaks marked with an asterisk are spinning sidebands.
Figure 14:
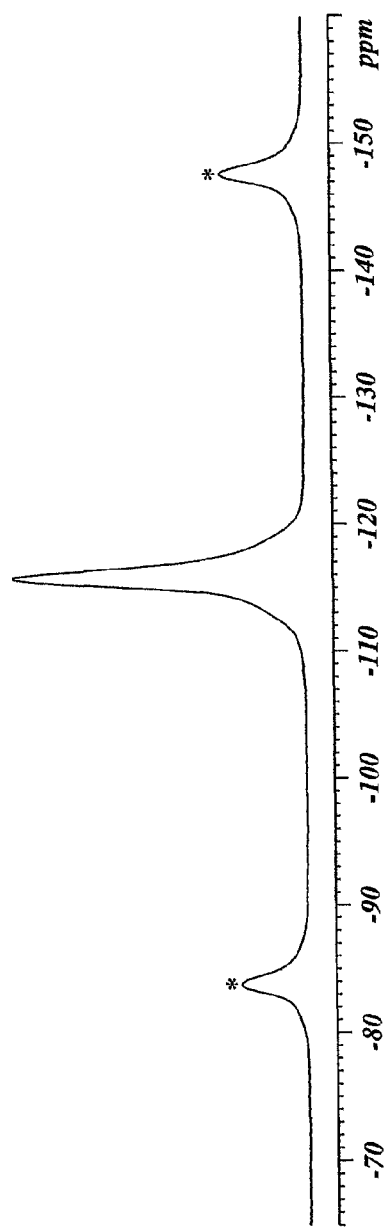
FIG. 14: Proton decoupled $^{19}$F MAS spectra of Form B atorvastatin magnesium. The peaks marked with an asterisk are spinning sidebands.
Figure 15:
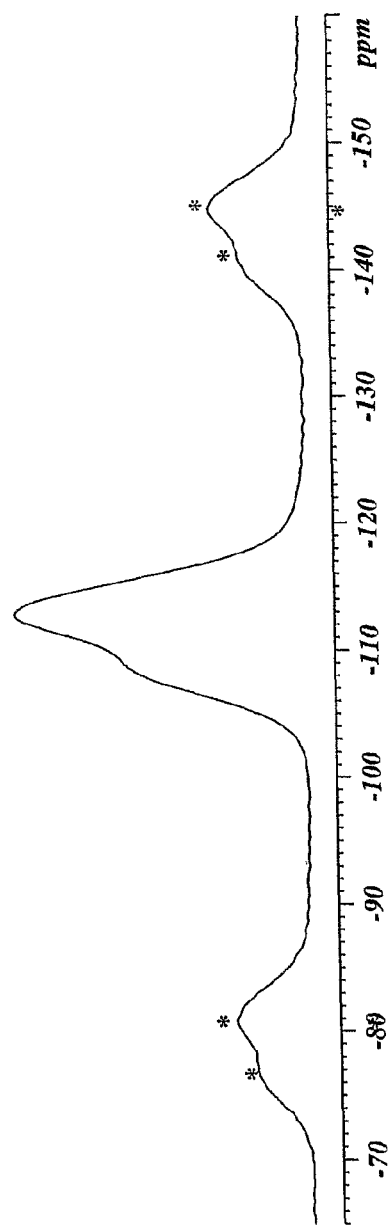
FIG. 15: Proton decoupled $^{19}$F MAS spectra of Form C atorvastatin magnesium. The peaks marked with an asterisk are spinning sidebands.
Figure 16:
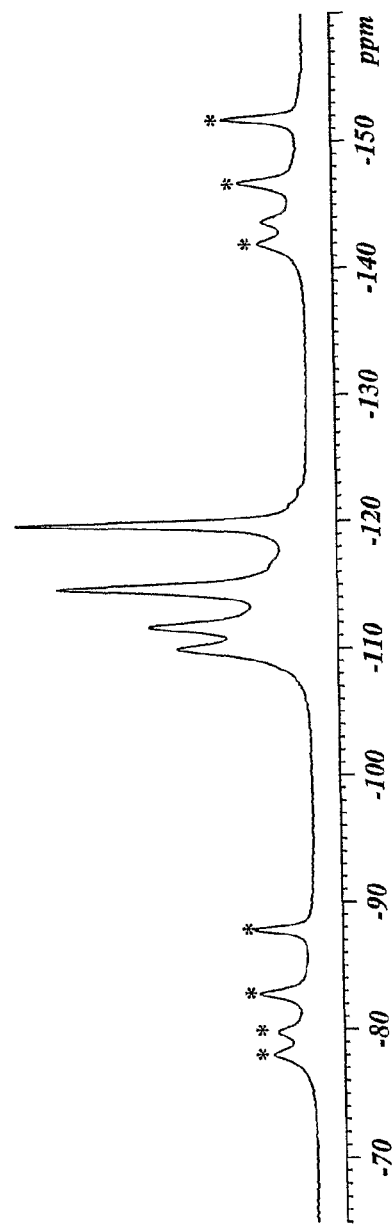
FIG. 16: Proton decoupled $^{19}$F MAS spectra of Form D atorvastatin magnesium. The peaks marked with an asterisk are spinning sidebands.
Figure 17:
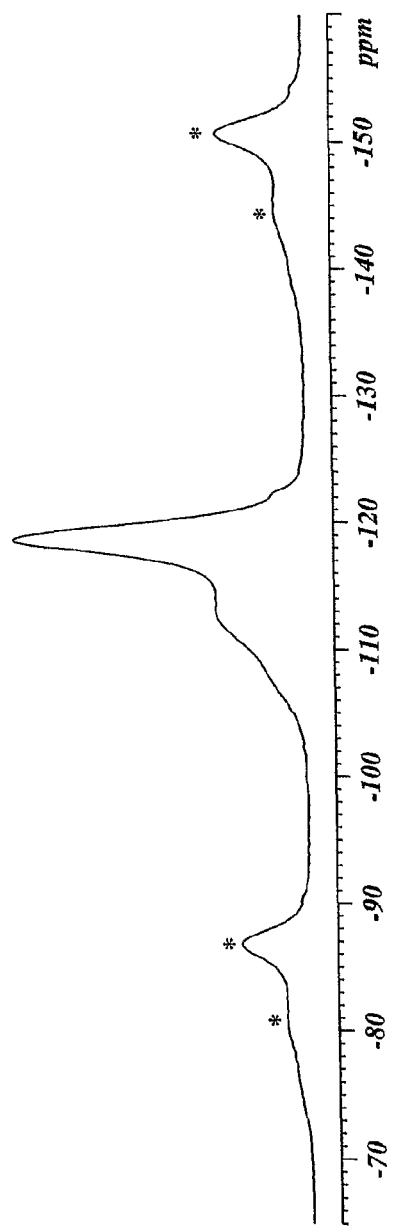
FIG. 17: Proton decoupled $^{19}$F MAS spectra of Form E atorvastatin magnesium. The peaks marked with an asterisk are spinning sidebands.
Figure 18:
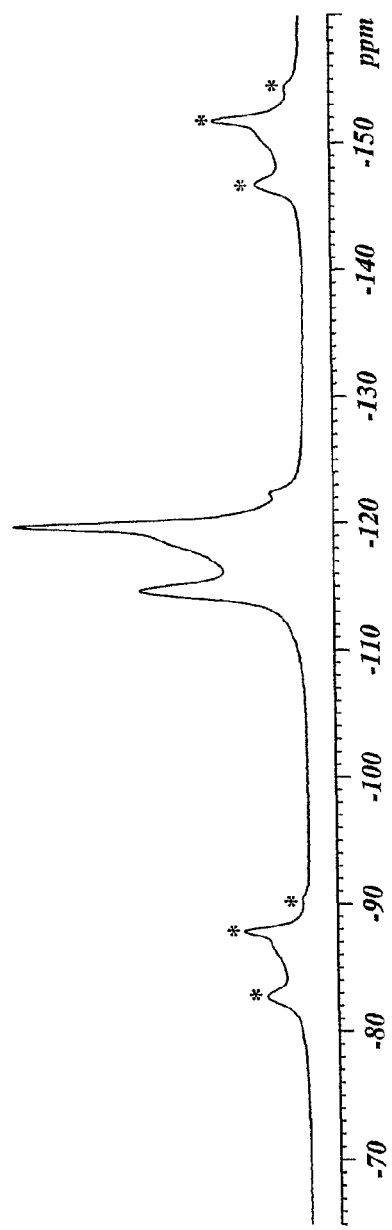
FIG. 18: Proton decoupled $^{19}$F MAS spectra of Form F atorvastatin magnesium. The peaks marked with an asterisk are spinning sidebands.

Form A, Form B, Form C, Form D, Form E, and Form F atorvastatin magnesium can be characterized by one or more of x-ray powder diffraction-, solid state NMR carbon chemical shift-, and solid state NMR fluorine chemical shift patterns.

The "forms" of atorvastatin magnesium disclosed in the present invention may exist as ordered crystals, disordered crystals, liquid crystals, plastic crystals, mesophases, and the like. In X-ray powder diffractograms forms that are related through disorder will have essentially the same major peak positions but the disordering process will cause broadening of these peaks. For many of the weaker peaks, the broadening may be so severe that they are no longer visible above the background. The peak broadening caused by disorder may in addition cause errors in the location of the exact peak position. For solid state nuclear magnetic resonance (SSNMR) spectra, significant differences in chemical shifts may be seen from crystalline to disordered phases.

EXPERIMENTAL

X-Ray Powder Diffraction

Form A, Form B, Form C, Form D, Form E, and Form F atorvastatin magnesium were characterized by their X-ray powder diffraction pattern. Thus, the X-ray powder diffraction patterns of Forms A, B, C, D, E, and F were carried out on a Bruker D8 Discover X-ray powder diffractometer with GADDS (General Area Diffraction Detector System) CS operating in reflection mode using CuK$_\alpha$ radiation. The tube voltage and amperage were set to 40 kV and 40 mA, respectively. Scans were collected with the sample to detector distance set at 15.0 cm. The samples were scanned for a period of 60 seconds covering a range of 4.5° to 38.7° in 2θ. The diffractometer was calibrated for peak positions in 2θ using a corundum standard. Samples were run in ASC-6 silicon sample holders purchased from Gem Dugout (State College, Pa.). All analyses were conducted at room temperature, which is generally 20°-30° C. Data were collected and integrated using GADDS for WNT software version 4.1.14T. Diffractograms were evaluated using DiffracPlus software, release 2003, with Eva version 8.0 (available from Bruker AXS, Inc., Madison, Wis.).

To perform an X-ray diffraction measurement on a Bruker D8 Discover X-ray powder diffractometer with GADDS CS used for measurements reported herein, the sample is typically placed into a cavity in the middle of the silicon sample holder. The sample powder is pressed by a glass slide or equivalent to ensure a random surface and proper sample height. The sample holder is then placed into the Bruker instrument and the powder x-ray diffraction pattern is collected using the instrumental parameters specified above. Measurement differences associated with such X-ray powder diffraction analyses result from a variety of factors including: (a) errors in sample preparation (e.g., sample height), (b) instrument errors (e.g. flat sample errors), (c) calibration errors, (d) operator errors (including those errors present when determining the peak locations), and (e) the nature of the material (e.g. preferred orientation and transparency errors). Calibration errors and sample height errors often result in a shift of all the peaks in the same direction. Small differences in sample height when using a flat holder will lead to large displacements in XRPD peak positions. A systematic study showed that a sample height difference of 1 mm lead to peak shifts as high as 1° 2θ (Chen et al.; J Pharmaceutical and Biomedical Analysis, 2001; 26,63). These shifts can be identified from the X-ray diffractogram and can be eliminated by compensating for the shift (applying a systematic correction factor to all peak position values) or recalibrating the instrument. As mentioned above, it is possible to rectify measurements from the various instruments by applying a systematic correction factor to bring the peak positions into agreement. In general, this correction factor will bring the measured peak positions into agreement with the expected peak positions and is in the range of the expected 2θ value±0.2° 2θ.

Tables 1-6 list peak positions in degrees 2θ, relative intensities, and relative peak widths for X-ray powder diffraction patterns of each form of atorvastatin magnesium disclosed in the present application. The relatively narrow peak positions were picked by the DiffracPlus with Eva version 8.0 software. The broader peak positions were visually determined. All peak positions were rounded to 0.1° 2θ. The following abbreviations are used in Tables 1-6 to describe the peak intensity (s=strong; m=medium; w=weak) and the peak width (b=broad (where broad refers to peak widths of between 0.2 and 1.0 degrees 2θ, sh=shoulder, vb=very broad (where very broad refers to peaks with >1 degrees 2θ peak width)).

TABLE 1

XPRD Peak List for Form A Atorvastatin magnesium

| degree 2θ ± 0.2 | Relative Intensity[a] | Relative Peak Width[b] |
|---|---|---|
| 9.3 | w | b |
| 11.7 | w | b |
| 14.3 | w | b |
| 18.4 | s | b |

TABLE 2

XPRD Peak List for Form B Atorvastatin magnesium

| degree 2θ ± 0.2 | Relative Intensity[a] | Relative Peak Width[b] |
|---|---|---|
| 5.3 | w | b |
| 6.1 | w | b |
| 8.0 | w | b |
| 9.1 | w | b |
| 10.5 | w | b, sh |
| 10.9 | m | b |
| 13.2 | w | b |
| 13.9 | w | b |
| 15.6 | m | b |
| 16.1 | w | b |
| 16.7 | w | b |
| 17.2 | w | b |
| 18.1 | s | b, sh |
| 18.4 | s | b |
| 19.8 | s | b |
| 20.7 | w | b, sh |
| 21.2 | m | b |
| 21.8 | m | b |
| 23.0 | w | b |
| 24.1 | w | b |
| 24.8 | w | b |
| 25.6 | w | b |
| 27.3 | w | b |
| 29.1 | w | b |

TABLE 3

XPRD Peak List for Form C Atorvastatin magnesium

| degree 2θ ± 0.2 | Relative Intensity[a] | Relative Peak Width[b] |
|---|---|---|
| 5.2 | w | b |
| 6.6 | w | b |
| 8.7 | s | b |
| 9.8 | w | b |
| 11.6 | m | b |
| 12.3 | m | b |
| 13.5 | m | b |
| 14.6 | m | b |
| 16.2 | m | b |
| 18.7 | s | vb |
| 19.9 | s | b, sh |
| 23.2 | s | vb |

TABLE 4

XPRD Peak List for Form D atorvastatin magnesium

| degree 2θ ± 0.2 | Relative Intensity[a] | Relative Peak Width[b] |
|---|---|---|
| 7.7 | m | b |
| 8.8 | m | b |
| 10.2 | m | b |
| 11.9 | w | b |
| 13.8 | w | b |
| 15.9 | s | b |
| 17.3 | m | b |
| 18.7 | s | b |
| 20.5 | s | vb |
| 24.2 | m | b |
| 26.7 | w | b |
| 30.6 | w | vb |

TABLE 5

XPRD Peak List for Form E atorvastatin magnesium

| degree 2θ ± 0.2 | Relative Intensity[a] | Relative Peak Width[b] |
|---|---|---|
| 8.4 | m | b |
| 10.0 | m | b |
| 11.1 | w | b |
| 12.4 | w | b |
| 14.0 | w | b |
| 16.6 | s | b |
| 17.9 | s | b |
| 20.2 | s | b |
| 22.0 | s | b, sh |
| 23.1 | s | b, sh |
| 26.3 | m | vb |
| 30.3 | m | vb |

TABLE 6

XPRD Peak List for Form F atorvastatin magnesium

| degree 2θ ± 0.2 | Relative Intensity[a] | Relative Peak Width[b] |
|---|---|---|
| 8.7 | m | b |
| 10.1 | s | b |
| 11.7 | w | b |
| 12.7 | w | b |
| 14.7 | w | b |
| 16.1 | s | b |
| 17.5 | m | b |
| 18.5 | m | b |
| 20.4 | s | b, sh |
| 21.4 | s | vb, sh |
| 23.7 | m | vb |
| 26.8 | w | vb |
| 30.4 | m | vb |

Table 7 lists combinations of 29 peaks for Forms A, B, C, D, E, and F atorvastatin magnesium, i.e., a set of x-ray diffraction lines that are unique to each form

| Form | degree 2θ ± 0.2 |
|---|---|
| A | 9.3 |
|  | 14.3 |
|  | 18.4 |

| Form | degree 2θ ± 0.2 |
|---|---|
| B | 6.1 |
|   | 8.0 |
|   | 10.9 |
|   | 19.8 |
|   | 23.0 |
| C | 5.2 |
|   | 6.6 |
|   | 12.3 |
| D | 7.7 |
|   | 20.5 |
|   | 24.2 |
| E | 8.4 |
|   | 16.6 |
|   | 17.9 |
| F | 8.7 |
|   | 10.1 |
|   | 11.7 |
|   | 16.1 |

Solid State NMR Spectroscopy

For both $^{13}C$—, and $^{19}F$ spectroscopy, approximately 80 mg of each sample were tightly packed into a 4 mm ZrO spinner. The spectra were collected at ambient conditions on a Bruker-Biospin 4 mm BL HFX CPMAS probe (Bruker BioSpin Corporation, 15 Fortune Drive, Manning Park, Billerica, Mass. 01821-3991) positioned into a wide-bore Bruker-Biospin Avance DSX 500 MHz NMR spectrometer. The samples were positioned at the magic angle and spun at 15.0 kHz, corresponding to the maximum specified spinning speed for the 4 mm spinners. The fast spinning speed minimized the intensities of the spinning side bands. The number of scans was adjusted to obtain adequate S/N.

$^{13}C$ Spectroscopy

The $^{13}C$ solid state spectra were collected using a proton decoupled cross-polarization magic angle spinning experiment (CPMAS). The Hartman-Hahn contact time was set to 2.0 ms. The proton decoupling field of approximately 90 kHz was applied. 2048 scans were collected. The recycle delay was adjusted to 7 seconds. The shift values are listed in Tables 8 to 13. The spectra were referenced using an external standard of crystalline adamantane, setting its upfield resonance to 29.5 ppm.

TABLE 8

Carbon chemical shifts in ppm of Form A atorvastatin magnesium

| $^{13}C$ Chemical Shifts[a] [ppm] ± 0.2 | Intensity[b] |
|---|---|
| 180.3 | 0.8 |
| 177.9 | 0.6 |
| 168.0 | 0.1 |
| 166.6 | 1.3 |
| 163.5 | 0.5 |
| 161.6 | 1.1 |
| 141.7 | 1.5 |
| 140.3 | 0.8 |
| 134.9 | 1.2 |
| 129.3 | 4.7 |
| 124.4 | 12.0 |
| 123.3 | 2.9 |
| 118.7 | 3.5 |
| 117.4 | 4.3 |
| 116.1 | 3.6 |
| 70.3 | 4.0 |
| 68.0 | 1.7 |
| 67.2 | 1.5 |

TABLE 8-continued

Carbon chemical shifts in ppm of Form A atorvastatin magnesium

| $^{13}C$ Chemical Shifts[a] [ppm] ± 0.2 | Intensity[b] |
|---|---|
| 42.3 | 1.5 |
| 36.4 | 4.2 |
| 26.6 | 0.1 |
| 22.2 | 4.2 |

TABLE 9

Carbon chemical shifts in ppm of Form B atorvastatin magnesium

| $^{13}C$ Chemical Shifts[a] [ppm] ± 0.2 | Intensity[b] |
|---|---|
| 183.5 | 1.2 |
| 180.4 | Peak shoulder |
| 178.7 | 0.8 |
| 166.0 | 2.3 |
| 163.6 | 1.4 |
| 161.7 | 2.0 |
| 139.3 | 5.0 |
| 136.1 | 5.2 |
| 133.8 | 4.6 |
| 132.2 | 3.4 |
| 129.6 | 12.0 |
| 126.8 | 4.5 |
| 125.4 | 4.3 |
| 122.9 | 1.5 |
| 120.9 | 1.8 |
| 119.7 | 1.8 |
| 118.3 | 1.7 |
| 115.8 | 4.4 |
| 72.9 | 2.8 |
| 71.0 | 5.0 |
| 45.6 | 2.2 |
| 43.3 | 6.8 |
| 41.6 | 5.4 |
| 41.0 | 5.5 |
| 27.1 | 5.4 |
| 26.9 | 5.1 |
| 24.9 | 3.6 |
| 24.3 | 4.0 |
| 22.1 | 1.9 |
| 19.5 | 8.9 |

TABLE 10

Carbon chemical shifts in ppm of Form C atorvastatin magnesium

| $^{13}C$ Chemical Shifts[a] [ppm] ± 0.2 | Intensity[b] |
|---|---|
| 180.6 | 0.8 |
| 179.9 | 0.8 |
| 167.6 | 1.4 |
| 163.3 | 1.1 |
| 161.5 | 1.4 |
| 141.2 | 0.9 |
| 139.1 | 1.6 |
| 135.3 | 4.6 |
| 133.3 | 3.9 |
| 129.2 | 12.0 |
| 126.3 | 4.3 |
| 123.1 | 3.8 |
| 119.7 | 3.6 |
| 117.8 | 3.5 |
| 116.0 | 3.1 |
| 71.1 | 1.6 |
| 67.6 | 1.3 |

TABLE 10-continued

Carbon chemical shifts in ppm of Form C atorvastatin magnesium

| $^{13}$C Chemical Shifts$^a$ [ppm] ± 0.2 | Intensity$^b$ |
|---|---|
| 43.1 | 3.5 |
| 42.4 | 3.5 |
| 26.6 | 3.4 |
| 22.4 | 4.4 |

TABLE 11

Carbon chemical shifts in ppm of Form D atorvastatin magnesium

| $^{13}$C Chemical Shifts$^a$ [ppm] ± 0.2 | Intensity$^b$ |
|---|---|
| 183.1 | 1.2 |
| 182.4 | 1.6 |
| 179.9 | 1.8 |
| 176.5 | 0.6 |
| 165.9 | 2.3 |
| 163.4 | 1.4 |
| 162.7 | 1.4 |
| 161.4 | 2.1 |
| 160.8 | 1.8 |
| 141.3 | 1.0 |
| 138.6 | 6.5 |
| 136.9 | 2.8 |
| 136.4 | 3.0 |
| 135.0 | 6.3 |
| 134.4 | 5.1 |
| 132.6 | 4.7 |
| 131.5 | 7.4 |
| 130.5 | 8.4 |
| 129.4 | 12.0 |
| 128.3 | 10.2 |
| 126.4 | 2.7 |
| 124.1 | 5.5 |
| 123.2 | 2.8 |
| 121.0 | 6.9 |
| 117.1 | 5.0 |
| 115.2 | 3.9 |
| 114.3 | 2.0 |
| 71.5 | 1.8 |
| 70.4 | 2.4 |
| 69.3 | 4.3 |
| 67.4 | 2.5 |
| 66.5 | 4.5 |
| 46.5 | 2.4 |
| 45.6 | 3.5 |
| 44.2 | 4.4 |
| 43.2 | 5.9 |
| 41.4 | 2.7 |
| 39.7 | 4.0 |
| 37.6 | 0.8 |
| 27.2 | 6.8 |
| 26.8 | 5.8 |
| 24.6 | 2.7 |
| 23.7 | 3.5 |
| 22.9 | 3.4 |
| 21.5 | 1.8 |
| 20.9 | 1.3 |
| 19.1 | 3.9 |

TABLE 12

Carbon chemical shifts in ppm of Form E atorvastatin magnesium

| $^{13}$C Chemical Shifts$^a$ [ppm] ± 0.2 | Intensity$^b$ |
|---|---|
| 181.0 | 0.8 |
| 166.4 | 2.2 |
| 162.6 | 1.4 |
| 160.7 | 1.9 |
| 137.8 | 5.0 |
| 135.2 | 8.5 |
| 131.5 | 6.1 |
| 129.6 | 11.0 |
| 128.9 | 12.0 |
| 123.8 | 3.9 |
| 122.0 | 3.6 |
| 117.7 | 2.6 |
| 115.6 | 1.7 |
| 114.9 | 1.6 |
| 67.9 | 1.7 |
| 67.0 | 1.9 |
| 43.2 | 3.9 |
| 41.7 | 2.7 |
| 41.1 | 2.6 |
| 26.6 | 5.3 |
| 24.0 | 4.3 |
| 21.0 | 3.6 |

TABLE 13

Carbon chemical shifts in ppm of Form F atorvastatin magnesium

| $^{13}$C Chemical Shifts$^a$ [ppm] ± 0.2 | Intensity$^b$ |
|---|---|
| 182.6 | 1.1 |
| 180.0 | 1.3 |
| 166.0 | 3.0 |
| 162.9 | 1.0 |
| 162.6 | 1.1 |
| 161.1 | 1.6 |
| 160.7 | 1.6 |
| 138.2 | 6.5 |
| 136.3 | 3.2 |
| 135.1 | 8.2 |
| 131.4 | 7.1 |
| 130.4 | 5.6 |
| 129.4 | 9.5 |
| 128.5 | 12.0 |
| 124.0 | 5.5 |
| 121.0 | 4.5 |
| 117.4 | 2.9 |
| 115.1 | 1.7 |
| 114.2 | 1.8 |
| 69.1 | 1.6 |
| 67.4 | 1.9 |
| 66.4 | 3.6 |
| 46.4 | 1.7 |
| 45.6 | 2.0 |
| 43.2 | 2.8 |
| 40.0 | 1.8 |
| 39.3 | 1.6 |
| 27.0 | 4.5 |
| 23.4 | 3.4 |
| 23.1 | 3.4 |
| 19.4 | 3.3 |

In each of Tables 8-13, "a" is referenced to external sample of solid phase adamantane at 29.5 ppm; and "b" is defined as peak height. Intensities can vary depending on the actual setup of the CPMAS experimental parameters and the thermal history of the sample. CPMAS intensities are not necessarily quantitative.

$^{19}$F Spectroscopy

The $^{19}$F solid state spectra were collected using a proton decoupled magic angle spinning (MAS) experiment. The proton decoupling field of approximately 90 kHz was applied. 32 scans were collected. The recycle delay was set to 90 seconds to ensure acquisition of quantitative spectra. Proton longitudinal relaxation times ($^1H\ T_1$) were calculated based on a fluorine detected proton inversion recovery relaxation experiment. Fluorine longitudinal relaxation times ($^{19}F\ T_1$) were calculated based on a fluorine detected fluorine inversion recovery relaxation experiment. The spectra were referenced using an external sample of trifluoro-acetic acid (50% V/V in $H_2O$), setting its resonance to −76.54 ppm. Tables 14 to 19 list the fluorine chemical shifts in ppm of Forms A, B, C, D, E, and F atorvastatin magnesium respectively.

TABLE 14

| $^{19}F$ Chemical Shifts [ppm] ± 0.2 |
| --- |
| −108.4 (shoulder) |
| −112.6 |

TABLE 15

| $^{19}F$ Chemical Shifts [ppm] ± 0.2 |
| --- |
| −115.7 |

TABLE 16

| $^{19}F$ Chemical Shifts [ppm] ± 0.2 |
| --- |
| −109.6 (shoulder) |
| −113.0 |

TABLE 17

| $^{19}F$ Chemical Shifts [ppm] ± 0.2 |
| --- |
| −110.0 |
| −111.7 |
| −114.7 |
| −119.8 |

TABLE 18

| $^{19}F$ Chemical Shifts$^a$ [ppm] ± 0.2 |
| --- |
| −113.2 |
| −118.8 |
| −122.1 (shoulder) |

TABLE 19

| $^{19}F$ Chemical Shifts [ppm] ± 0.2 |
| --- |
| −114.7 |
| −118.8 (shoulder) |
| −119.8 |
| −122.3 |

The forms of atorvastatin magnesium described herein may exist in anhydrous forms as well as containing various amounts of water and/or solvents. Anhydrous, hydrated and solvated forms of atorvastatin magnesium are intended to be encompassed within the scope of the present invention. The forms of atorvastatin magnesium described herein, regardless of the extent of water and/or solvent having equivalent x-ray powder diffractograms are within the scope of the present invention.

The new forms of atorvastatin magnesium described herein have advantageous properties.

The ability of a material to form good tablets at commercial scale depends upon a variety of physical properties of the drug, such as, for example, the Tableting Indices described in Hiestand H. and Smith D., Indices of Tableting Performance, Powder Technology, 1984, 38; 145-159. These indices may be used to identify forms of atorvastatin magnesium which have superior tableting performance. One such index is the Brittle Fracture Index (BFI), which reflects brittleness, and ranges from 0 (good-low brittleness) to 1 (poor high brittleness).

The present invention provides a process for the preparation of Forms A, B, C, D, E and F atorvastatin magnesium which comprises forming atorvastatin magnesium (e.g., from a solution or slurry in solvents) under conditions which yield Forms A, B, C, D, E and F atorvastatin magnesium.

The precise conditions under which Forms A, B, C, D, E and F atorvastatin magnesium are formed may be empirically determined and described herein are methods which have been found to be suitable in practice.

The compounds of the present invention can be prepared and administered in a wide variety of oral and parenteral dosage forms. The compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulation material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from two or ten to about seventy percent of the active compound. Suitable carriers are magnesium carbonate, methylcellulose, sodium carboxymethylcellulose, a low melting wax, cocoa butter, and the like. The term 'preparation' is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidfy.

Liquid form preparations include solutions, suspensions, retention enemas, and emulsions, for example water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dosage preparation may be varied or adjusted from 0.5 mg to 100 mg, preferably 2.5 to 80 mg according to the particular application and the potency of the active component. The composition can, if desired, also contain other compatible therapeutic agents.

In therapeutic use as hypolipidemic and/or hypocholesterolemic agents and agents to treat BPH, osteoporosis, and Alzheimer's disease, the Forms A, B, C, D, E, and F atorvastatin magnesium utilized in a method of this invention are administered at the initial dosage of about 2.5 mg to about 80 mg daily. Useful daily doses includes those in the range of about 2.5 mg to about 20 mg. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

Form A of atorvastatin magnesium may be prepared by dissolving the lactone form of atorvastatin (U.S. Pat. No. 5,273,995) in a solvent in which both the lactone and sodium salt forms are soluble. Useful solvents include lower weight alcohols, such as methanol and ethanol, water or tetrahydrofuran (THF) or mixtures thereof. NaOH is added to the solution, with stirring, at a temperature from about 45° C. to about 55° C., followed by slow addition of a magnesium salt, such as $MgCl_2$ or a hydrated form thereof. The mixture can them be cooled to ambient temperature to yield a suspension and a precipitate, which can be filtered from the suspension. Water can then be slowly added to the resulting solution with stirring to produce a second precipitate of atorvastatin magnesium Form A, which can then be removed by filtration.

Atorvastatin magnesium Form B may be prepared by suspending a sample of Form A, discussed above, in an aromatic organic solvent, such as benzene, xylene, ortho-xylene, para-xylene, meta-xylene, toluene, etc., at a temperature from about 40° C. to about 80° C. and stirring until From B atorvastatin magnesium is obtained.

Atorvastatin magnesium Form C may be obtained by suspending a sample of Form A, described above, in a mixture of acetonitrile and water at ambient temperature, with the acetonitrile being no more than 80% but no less than 50% of the acetonitrile/water mixture (volume/volume). The resulting mixture may then be stirred at ambient temperature until Form C is produced.

Form D atorvastatin magnesium may be prepared by suspending a sample of Form A, described above, in a mixture of about 9/1 (volume/volume) 2-propanol/water at ambient temperature and stirring the resulting mixture until Form D is obtained.

Form E atorvastatin magnesium may be prepared by suspending a sample of Form A, described above, in water at ambient temperature and stirring until Form E is obtained.

Form F atorvastatin magnesium may be obtained by suspending a sample of Form A, described above, in water at a temperature from about 45° C. to about 100° C. and stirring the resulting mixture until Form F is obtained.

Those skilled in the art will understand the forms of atorvastatin magnesium will be obtained in different amounts depending upon the amount of time spent in the steps above. Amounts of the desired forms may be obtained in periods from one day to 50 days by the methods above. It will also be understood that methods known in the art may be used to obtain the desired atorvastatin magnesium material from the resulting suspension, such as centrifuge filtration.

The following nonlimiting examples illustrate methods for preparing the compounds of the invention:

Example 1

[R—(R*,R*)]-2-(4-fluorophenyl)-β,δ-dihydroxy-5-(1-methylethyl)-3-phenyl-4-[(phenylamino)carbonyl]–1H-pyrrole-1-heptanoic acid hemi magnesium salt (Forms A, B, C, D, E, and F atorvastatin magnesium)

Form A Atorvastatin Magnesium

A 6.0 g sample of the lactone form of atorvastatin (U.S. Pat. No. 5,273,995) was dissolved in 100 mL of methanol at room temperature. Approximately 11.8 mL of 1N NaOH (1.05 mol equivalents) was then added to the mixture. The solution was then stirred at 50° C. for approximately 1 hour. A solution of 1.19 g $MgCl_2.6H_2O$ in 5 mL of $H_2O$ (0.55 mol equivalents) was then slowly added to the reaction mixture. The mixture was then cooled to room temperature and the resulting precipitate was removed by vacuum filtration through a 0.45-μm nylon membrane filter. Approximately 100 mL of $H_2O$ was then slowly added to the filtered solution, which caused a white precipitate to form. The resulting suspension was then stirred for approximately 30 minutes. The solid sample was then isolated by vacuum filtration. The filtered solid was then dried under vacuum at 70° C. for approximately 2 hours to afford 5.8 g of Form A atorvastatin magnesium.

Form B Atorvastatin Magnesium

A 50 mg sample of Form A atorvastatin magnesium (prepared as described above) was slurried in 0.25 mL of ortho-xylene at 45° C. for 28 days using magnetic stirring at 400 rpm. The solid sample was then isolated by centrifuge filtration through a 0.45-μm nylon membrane filter. The filtered solid was then air dried under ambient conditions for approximately 5 hours to afford Form B atorvastatin magnesium.

Form C Atorvastatin Magnesium

A 50 mg sample of Form A atorvastatin magnesium (prepared as described above) was slurried in 0.75 mL of acetonitrile:water (8:2, v/v) at ambient temperature for 28 days using magnetic stirring at 300 rpm. The solid sample was then isolated by centrifuge filtration through a 0.45-μm nylon membrane filter. The filtered solid was then air dried under ambient conditions for approximately 5 hours to afford Form C atorvastatin magnesium.

Form D Atorvastatin Magnesium

A 50 mg sample of Form A atorvastatin magnesium (prepared as described above) was slurried in 1 mL of 2-propanol:water (9:1, v/v) at ambient temperature for 28 days using magnetic stirring at 300 rpm. The solid sample was then isolated by centrifuge filtration through a 0.45-μm nylon membrane filter. The filtered solid was then air dried under ambient conditions for approximately 5 hours to afford Form D atorvastatin magnesium.

Form E Atorvastatin Magnesium

A 50 mg sample of Form A atorvastatin magnesium (prepared as described above) was slurried in 3 mL of water at ambient temperature for 28 days using magnetic stirring at 300 rpm. The solid sample was then isolated by centrifuge filtration through a 0.45-μm nylon membrane filter. The filtered solid was then air dried under ambient conditions for approximately 5 hours to afford Form E atorvastatin magnesium.

Form F Atorvastatin Magnesium

A 50 mg sample of Form A atorvastatin magnesium (prepared as described above) was slurried in 1 mL of water at 45° C. for 28 days using magnetic stirring at 300 rpm at 400 rpm. The solid sample was then isolated by centrifuge filtration through a 0.45-μm nylon membrane filter. The filtered solid was then air dried under ambient conditions for approximately 5 hours to afford Form F atorvastatin magnesium.

The claimed invention is:

1. A Form B atorvastatin magnesium having an X-ray powder diffraction containing the following 2θ values measured using $CuK_a$ radiation: 6.1, 8.0, 10.9, 19.8, and 23.0.

2. A Form B atorvastatin magnesium having a solid state NMR shift selected from the group consisting of:
 A) a $^{13}C$ shift containing values: 118.3, 125.4, 126.8, 132.2, and 133.8 ppm; and
 B) an $^{19}F$ shift containing value: −115.7 ppm.

3. A Form C atorvastatin magnesium having an X-ray diffraction containing the following 2θ values measured using $CuK_a$ radiation: 5.2, 6.6, and 12.3.

4. A Form C atorvastatin magnesium having a solid state NMR shift selected from the group consisting of:
 A) a $^{13}C$ shift containing the values: 129.2, 133.3, and 139.1 ppm; and
 B) an $^{19}F$ shift containing the values: −109.6, and −113.0 ppm.

5. A Form D atorvastatin magnesium having an X-ray diffraction containing the following 2θ values measured using $CuK_a$ radiation: 7.7, 20.5, and 24.2.

6. A Form D atorvastatin magnesium having a solid state NMR shift selected from the group consisting of:
 A) a $^{13}C$ shift containing the values: 132.6, 134.4, 136.9, and 138.6 ppm; and
 B) an $^{19}F$ shift containing the values: −110.0, −111.7, −114.7, and −119.8 ppm.

7. A Form F atorvastatin magnesium having an X-ray diffraction containing the following 2θ values measured using $CuK_a$ radiation: 8.7, 10.1, 11.7, and 16.1.

8. A Form F atorvastatin magnesium having a solid state NMR shift selected from the group consisting of:
 A) a $^{13}C$ shift containing the values: 128.5, 130.4, and 138.2 ppm; and
 B) an $^{19}F$ shift containing the values: −114.7, −118.8, −119.8, and −122.3 ppm.

9. A pharmaceutical composition comprising atorvastatin magnesium selected from the group consisting of Form B, Form C, Form D, and Form F; and at least one pharmaceutically acceptable excipient, diluent, or carrier.

10. A Form B atorvastatin magnesium having an X-ray powder diffraction containing the following 2θ values measured using $CuK_a$ radiation: 5.3, 6.1, 8.0, 9.1, 10.5, 10.9, 13.2, 13.9, 15.6, 16.1, 16.7, 17.2, 18.1, 18.4, 19.8, 20.7, 21.2, 21.8, 23.0, 24.1, 24.8, 25.6, 27.3, and 29.1.

11. A Form B atorvastatin magnesium having a solid state NMR spectrum containing the following $^{13}C$ chemical shift values: 19.5, 22.1, 24.3, 24.9, 26.9, 27.1, 41.0, 41.6, 43.3, 45.6, 71.0, 72.9, 115.8, 118.3, 119.7, 120.9, 122.9, 125.4, 126.8, 129.6, 132.2, 133.8, 136.1, 139.3, 161.7, 163.6, 166.0, 178.7, 180.4, and 183.5 ppm.

12. A Form B atorvastatin magnesium having a solid state NMR spectrum containing the following $^{13}C$ chemical shift values: 118.3, 125.4, 126.8, 132.2, and 133.8 ppm.

13. A Form B atorvastatin magnesium having a solid state NMR spectrum containing the following $^{19}F$ chemical shift values: −115.7 ppm.

14. A Form C atorvastatin magnesium having an X-ray powder diffraction containing the following 2θ values measured using $CuK_a$ radiation: 5.2, 6.6, 8.7, 9.8, 11.6, 12.3, 13.5, 14.6, 16.2, 18.7, 19.9, and 23.2.

15. A Form C atorvastatin magnesium having a solid state NMR spectrum containing the following $^{13}C$ chemical shift values: 22.4, 26.6, 42.4, 43.1, 67.6, 71.1, 116.0, 117.8, 119.7, 123.1, 126.3, 129.2, 133.3, 135.3, 139.1, 141.2, 161.5, 163.3, 167.6, 179.9, and 180.6 ppm.

16. A Form C atorvastatin magnesium having a solid state NMR spectrum containing the following $^{13}C$ chemical shift values: 129.2, 133.3, and 139.1 ppm.

17. A Form C atorvastatin magnesium having a solid state NMR spectrum containing the following $^{19}F$ chemical shift values: −109.6, and −113.0 ppm.

18. A Form D atorvastatin magnesium having an X-ray powder diffraction containing the following 2θ values measured using $CuK_a$ radiation: 7.7, 8.8, 10.2, 11.9, 13.8, 15.9, 17.3, 18.7, 20.5, 24.2, 26.7, and 30.6.

19. A Form D atorvastatin magnesium having a solid state NMR spectrum containing the following $^{13}C$ chemical shift values: 19.1, 20.9, 21.5, 22.9, 23.7, 24.6, 26.8, 27.2, 37.6, 39.7, 41.4, 43.2, 44.2, 45.6, 46.5, 66.6, 67.4, 69.3, 70.4, 71.5, 114.3, 115.2, 117.1, 121.0, 123.2, 124.1, 126.4, 128.3, 129.4, 130.5, 131.5, 132.6, 134.4, 135.0, 136.4, 136.9, 138.6, 141.3, 160.8, 161.4, 162.7, 163.4, 165.9, 176.5, 179.9, 182.4, and 183.1 ppm.

20. A Form D atorvastatin magnesium having a solid state NMR spectrum containing the following $^{13}C$ chemical shift values: 132.6, 134.4, 136.9, and 138.6 ppm.

21. A Form D atorvastatin magnesium having a solid state NMR spectrum containing the following $^{19}F$ chemical shift values: −110.0, −111.7, −114.7, and −119.8 ppm.

22. A Form F atorvastatin magnesium having an X-ray powder diffraction containing the following 2θ values measured using $CuK_a$ radiation: 8.7, 10.1, 11.7, 12.7, 14.7, 16.1, 17.5, 18.5, 20.4, 21.4, 23.7, 26.8, and 30.4.

23. A Form F atorvastatin magnesium having a solid state NMR spectrum containing the following $^{13}C$ chemical shift values: 19.4, 23.1, 23.4, 27.0, 39.3, 40.0, 43.2, 45.6, 46.4, 66.4, 67.4, 69.1, 114.2, 115.1, 117.4, 121.0, 124.0, 128.5, 129.4, 130.4, 131.4, 135.1, 136.3, 138.2, 160.7, 161.1, 162.6, 162.9, 166.0, 180.0, and 182.6 ppm.

24. A Form F atorvastatin magnesium having a solid state NMR spectrum containing the following $^{13}$C chemical shift values: 128.5, 130.4, and 138.2 ppm.

25. A Form F atorvastatin magnesium having a solid state NMR spectrum containing the following $^{19}$F chemical shift values: −114.7, −118.8, −119.8, and −122.3 ppm.

* * * * *